United States Patent
Hu et al.

(10) Patent No.: US 11,802,840 B2
(45) Date of Patent: Oct. 31, 2023

(54) INTELLIGENT INSTANT QUANTITATIVE TESTING DEVICE FOR MYCOTOXIN QUANTUM DOT TEST STRIP

(71) Applicant: Institute of Oilseed Crops, Chinese Academy of Agricultural Sciences, Wuhan (CN)

(72) Inventors: Xiaofeng Hu, Wuhan (CN); Zhaowei Zhang, Wuhan (CN); Peiwu Li, Wuhan (CN); Jun Jiang, Wuhan (CN); Wen Zhang, Wuhan (CN)

(73) Assignee: Institute of Oilseed Crops, Chinese Academy of Agricultural Sciences, Wuhan (CN)

( * ) Notice: Subject to any disclaimer, the term of this patent is extended or adjusted under 35 U.S.C. 154(b) by 0 days.

(21) Appl. No.: 18/083,601

(22) Filed: Dec. 19, 2022

(65) Prior Publication Data
US 2023/0266251 A1    Aug. 24, 2023

(30) Foreign Application Priority Data
Dec. 20, 2021  (CN) .......................... 202111567485.9

(51) Int. Cl.
*G01N 21/84*  (2006.01)
*G01N 21/78*  (2006.01)
*G01N 21/77*  (2006.01)

(52) U.S. Cl.
CPC ......... *G01N 21/8483* (2013.01); *G01N 21/78* (2013.01); *G01N 2021/7759* (2013.01); *G01N 2021/7786* (2013.01)

(58) Field of Classification Search
CPC .............. G01N 21/8483; G01N 21/78; G01N 2021/7759; G01N 2021/7786
See application file for complete search history.

(56) References Cited

U.S. PATENT DOCUMENTS

| 2008/0200562 A1 | 8/2008 | Yin et al. |
| 2012/0061586 A1* | 3/2012 | Yao .................... G01N 21/6486 |
| | | 250/461.1 |

FOREIGN PATENT DOCUMENTS

| CN | 105044346 A | 11/2015 |
| CN | 106153929 A | 11/2016 |

(Continued)

OTHER PUBLICATIONS

Translation of CN 105044346 A, Fang, Wei-huan, Nov. 11, 2015 (Year: 2015).*

(Continued)

*Primary Examiner* — Samuel P Siefke
*Assistant Examiner* — Henry H Nguyen
(74) *Attorney, Agent, or Firm* — Zhigang Ma (57) ABSTRACT

The present disclosure discloses an intelligent point-of-care testing device for mycotoxins based on a quantum dots test strip. A first light source and a second light source are used for exciting a test strip which is placed in a shell and coated with a mycotoxin antigen to obtain emitted light, and a light filtering component is used for filtering out impurity light. A clamping mechanism is used for clamping and fixing an image capturing component. The image capturing component is used for capturing, an image of mycotoxins based on a quantum dots test strip. A processor is used for analyzing and calculating image information to obtain a mycotoxin content result. The testing time is shortened, and the portability and practicability of mycotoxin testing are improved. Quantitative instant testing of single or multi-toxin mixed pollution is achieved, and the technical problem of fluorescence quantification is solved.

5 Claims, 6 Drawing Sheets

Specification includes a Sequence Listing.

(56) References Cited

FOREIGN PATENT DOCUMENTS

| CN | 107884571 | A | | 4/2018 |
|---|---|---|---|---|
| CN | 207442978 | U | * | 6/2018 |
| CN | 111781186 | A | | 10/2020 |
| CN | 112326959 | A | | 2/2021 |
| CN | 214150449 | U | | 9/2021 |

OTHER PUBLICATIONS

Translation of CN 107884571 A, Zhang, Lei, Apr. 6, 2018 (Year: 2018).*
Translation of CN 111781186 A, Song, Chun-yuan, Oct. 16, 2020 (Year: 2020).*
Translation of CN 21450449 U, Liu, Zi-mao, Sep. 7, 2021 (Year: 2021).*

* cited by examiner

FIG. 6

INTELLIGENT INSTANT QUANTITATIVE TESTING DEVICE FOR MYCOTOXIN QUANTUM DOT TEST STRIP

REFERENCE TO SEQUENCE LISTING

The substitute sequence listing is submitted as a XML file filed via EFS-Web, with a file name of "Substitute_Sequence_Listing_HBCR-U.S. Pat. No. 1,224,262.XML", a creation date of May 4, 2023, and a size of 10146 bytes. The substitute sequence Listing filed via EFS-Web is a part of the specification and is incorporated in its entirety by reference herein.

TECHNICAL FIELD

The present disclosure relates to the technical field of mycotoxin testing, particularly an intelligent point-of-care testing device for mycotoxins based on a quantum dots test strip.

BACKGROUND

Food safety is a significant issue related to the national economy and the people's livelihood. Food is vulnerable to mixed pollution of a variety of mycotoxins, which seriously threatens people's life, health, and economic and trade security. Mycotoxins are a secondary metabolite produced by fungi and one of the most dangerous food pollutants naturally produced. About 4.5 billion people worldwide have been exposed to mycotoxins for a long time. More than 300 kinds of mycotoxins have been isolated and identified, among which, aflatoxin B1 (AFB1) has been identified as a class of carcinogens by the International Agency for Research on Cancer (IARC), which can induce liver cancer and has teratogenic and mutagenic effects. Ochratoxin (OTA) is nephrotoxic and can cause urinary cancer. The IARC has identified OTA as a Class II carcinogen. Zearalenone (ZEN) has an estrogen effect, which can lead to poor semen quality and impaired reproductive function. Mycotoxin contamination is severe, which easily causes acute or chronic diseases of people and animals, resulting in major food safety problems. According to research, as the climate changes, crops will be polluted by more mycotoxins in the future, most of which are mixed pollution. Mycotoxins are naturally produced, and mixed mycotoxin pollution can occur in various links such as seeding, harvesting, storage, and transportation of grains. Therefore, establishing a highly sensitive and intelligent instant testing technology for mixed mycotoxin pollution is urgently needed to ensure food quality and safety and promote the high-quality development of the food industry.

Mycotoxin testing methods mainly include biological identification, chemical analysis, and large-scale instrument analysis. The biological identification method is a traditional method for the identification of mycotoxins, in which, whether mycotoxins really exist is detected mainly according to the fact that mycotoxins can affect the cells of poultry, microorganisms, aquatic organisms, and other organisms. This traditional method has poor specificity and low sensitivity and cannot achieve quantification. Usually, this traditional method is only used as an evidence for chemical analysis. The chemical analysis method mainly uses thin-layer chromatography to isolate and analyze mycotoxins, and can realize purification of the mycotoxins. The chemical method is simple in operation and low in cost, and has been written into the national standard. However, due to the use of many solvents and the risk of direct contact with toxins by operators, this method has been phased out. Large-scale instrument analysis technology is currently a mainstream mycotoxin analysis method, such as high-performance liquid chromatography (HPLC) and liquid chromatography-tandem mass spectrometry (LC-MS/MS). Due to high sensitivity, accurate determination results, good specificity and the like, HPLC and LC-MS/MS have become the standard methods for mycotoxin testing in the United States, the European Union (European Committee for Standardization ENISO16050:2011) and other countries and regions in the world. They have been widely used in foods and feeds. However, mycotoxin levels can vary during laboratory testing, such as storage, sample transfer, and sample pre-processing. That is not conducive to on-site supervision and rapid emergency treatment.

To meet the demand of market supervision for instant testing of mycotoxins in agricultural products, developing an intelligent instant testing device with a higher testing speed and better portability is of significant research and application value.

SUMMARY

The present disclosure provides an intelligent point-of-care testing device for mycotoxins based on a quantum dots test strip to achieve technical effects of higher testing speed and better portability.

The present disclosure provides an intelligent point-of-care testing device for mycotoxins based on a quantum dots test strip, including a shell, a first light source, a second light source, a light filtering component, a clamping component, an image capturing component, and a processor. The first light source and the second light source are both arranged inside the shell. The first light source and the second light sources are opposite to the test strip in the shell and coated with a mycotoxin antigen coupled with a hyperbranched DNA tetrahedron suspension nanomaterial. A top opening is arranged at a top of the shell. The light filtering component blocks the top opening. The clamping mechanism is located above the top of the shell. The image capturing component is arranged in the clamping mechanism, and a camera of the image capturing component is opposite to the light filtering component. A signal output end of the image capturing component is in communication with a signal input end of the processor.

Specifically, the processor includes:
an image receiving module, configured to receive an image output by the image capturing component;
an image processing module, configured to obtain a fluorescent region of test line T and a fluorescent region of control line C according to the image, and obtaining red values, green values and blue values of the fluorescent region of test line T and the fluorescent region of control line C respectively;
a normalization module, configured to normalize the red values, green values and blue values of the fluorescent region of test line T and the fluorescent region of control line C to obtain a color normalized value $F_T$ of test line T and a color normalized value $F_C$ of control line C; and
an operation module, configured to calculate a mycotoxin content value X according to a standard curve equation $Y=a*\ln(X)+b$, where Y represents a ratio of $F_T$ to $F_C$; a represents a slope of a standard curve linearly fitted according to standard points; and b represents an intercept of the standard curve linearly fitted according to the standard points on the y-axis.

Specifically, the normalization module includes:

a normalization unit, configured to traverse the red values, the green values and the blue values of pixel points of a preset test strip central region row by row, perform normalization to obtain a color normalized value F of each pixel point, and calculate an average value Fa of the color normalized values of the pixel points of each row;

a unit for determining a color normalized value $F_T$ of test line T, configured to determine whether the average value of the color normalized values of the pixel points of certain row A is greater than the average value of the color normalized values of the pixel points of the previous row by a preset threshold; mark row A as a start point of line T if yes; continue to determine whether the average value of the color normalized values of the pixel points of certain row B behind row A is greater than the average value of the color normalized values of the pixel points of the latter row by the preset threshold; mark row B as an end point of line T if yes; and calculate an average value, i.e. the color normalized value $F_T$ of test line T, of the color normalized values of all the pixel points between row A and row B; and a unit for determining a color normalized value $F_C$ of control line C, configured to determine whether the average value of the color normalized values of the pixel points of certain row C behind row B is greater than the average value of the color normalized values of the pixel points of the previous row by the preset threshold; mark row C as a start point of line C if yes; continue to determine whether the average value of the color normalized values of the pixel points of certain row D behind row C is greater than the average value of the color normalized values of the pixel points of the latter row by the preset threshold; mark row D as an end point of line C if yes; and calculate an average value, i.e. the color normalized value $F_C$ of control line C, of the color normalized values of all the pixel points between row C and row D.

Specifically, the first light source and the second light source are arranged in the shell in a manner of forming an included angle β. The β is determined according to $$\tan\left(90 - \frac{\beta + 45}{2}\right) = \frac{s - d}{2h},$$

where s is a transverse distance between the first light source and the second light source; d is a transverse distance of the emitted light of the first light source or the second light source irradiating the test strip region; and h is a perpendicular distance from the first light source or the second light source to the test strip region.

Specifically, the clamping mechanism includes a first L-shaped splint, a second L-shaped splint, an elastic component, a first bulge, a second bulge, a first elastic base, a second elastic base, and a cavity body. The first L-shaped splint and the second L-shaped splint are respectively arranged on both sides of the cavity body. A horizontal portion of the first L-shaped splint is connected with a horizontal portion of the second L-shaped splint through the elastic component. The elastic component passes through the cavity body. Both ends of an upper wall of the cavity body are respectively provided with a first opening and a second opening. The first bulge is vertically arranged on the first elastic base, and the first elastic base is arranged on the horizontal portion of the first L-shaped split. The second bulge is vertically arranged on the second elastic base, and the second elastic base is arranged on the horizontal portion of the second L-shaped split.

Specifically, inner walls of the first L-shaped split and the second L-shaped split are provided with antiskid flexible materials.

Specifically, the mycotoxin antigen coupled with a hyperbranched DNA tetrahedron suspension nanomaterial on the test strip is prepared by coupling a hyperbranched high-molecular polymer with a DNA tetrahedron connected with an initiator and then coupling the whole with an antigen.

Specifically, the preparation achieved by coupling a hyperbranched high-molecular polymer with a DNA tetrahedron connected with an initiator and then coupling the whole with an antigen includes:

enabling reaction between polyethylene glycol methyl ether methacrylate high-molecular polymer having a side chain and the DNA tetrahedron connected with an initiator at 95° C. for 2-3 minutes, and then performing quenching in an ice bath for 30 seconds to 1 minute for coupling to form the DNA tetrahedron suspension nanomaterial;

coupling a mycotoxin antigen to the DNA tetrahedron suspension nanomaterial to obtain a DNA tetrahedron suspension nanomaterial-antigen conjugate; and spraying the DNA tetrahedron suspension nanomaterial-antigen conjugate to line T of the test strip.

Specifically, after the spraying the DNA tetrahedron suspension nanomaterial-antigen conjugate to line T of the test strip, the preparation further includes:

drying the coated test strip in a vacuum drying oven at 38° C. for 30-60 minutes.

One or more technical solutions provided in the present disclosure at least have the following technical effects or advantages:

The first light source and the second light source are used for exciting the test strip which is placed in the shell and coated with the mycotoxin antigen coupled with the hyperbranched DNA tetrahedron suspension nanomaterial to obtain the emitted light, and the light filtering component is used for filtering out the impurity light. The clamping mechanism is used for clamping and fixing the image capturing component. The image capturing component is used for capturing an image of the quantum dots test strip. The processor is used for analyzing and calculating image information to obtain a mycotoxin content result. The traditional testing method is not used. The testing time is shortened, and the portability and practicability of mycotoxin testing are improved. Quantitative instant testing of multi-toxin mixed pollution is achieved, and the technical problem of fluorescence quantification is solved.

In the drawings: 1: shell; 2: first light source; 3: second light source; 4: light filtering component; 5: clamping mechanism; 6: first L-shaped splint; 7: second L-shaped splint; 8: elastic component; 9: first bulge; 10: second bulge; 11: first elastic base; 12: second elastic base; 13: cavity body; 14: light shield door; 15: battery; 16: power switch; 17: test strip clamping slot; 18: first opening; and 19: second opening.

DETAILED DESCRIPTION OF THE EMBODIMENTS

An embodiment of the present disclosure provides an intelligent point-of-care testing device for mycotoxins based on a quantum dots test strip to achieve technical effects of higher testing speed and better portability.

The general thought of the technical solutions in the embodiments of the present disclosure for achieving the above technical effects is as follows:

The first light source and the second light source are used for exciting the test strip which is placed in a shell and coated with the mycotoxin antigen coupled with the hyperbranched DNA tetrahedron suspension nanomaterial to obtain the emitted light, and the light filtering component is used for filtering out the impurity light. The clamping mechanism is used for clamping and fixing the image capturing component. The image capturing component is used for capturing an image of the mycotoxin quantum dots test strip. The processor is used for analyzing and calculating image information to obtain a mycotoxin content result. The traditional testing method is not used. The testing time is shortened, and the portability and practicability of mycotoxin testing are improved. Quantitative instant testing of multi-toxin mixed pollution is achieved, and the technical problem of fluorescence quantification is solved.

In order to better understand the above technical solution, the above technical solution will be described in detail below with reference to the accompanying drawings and specific implementation manners of the present disclosure.

Figure 1:
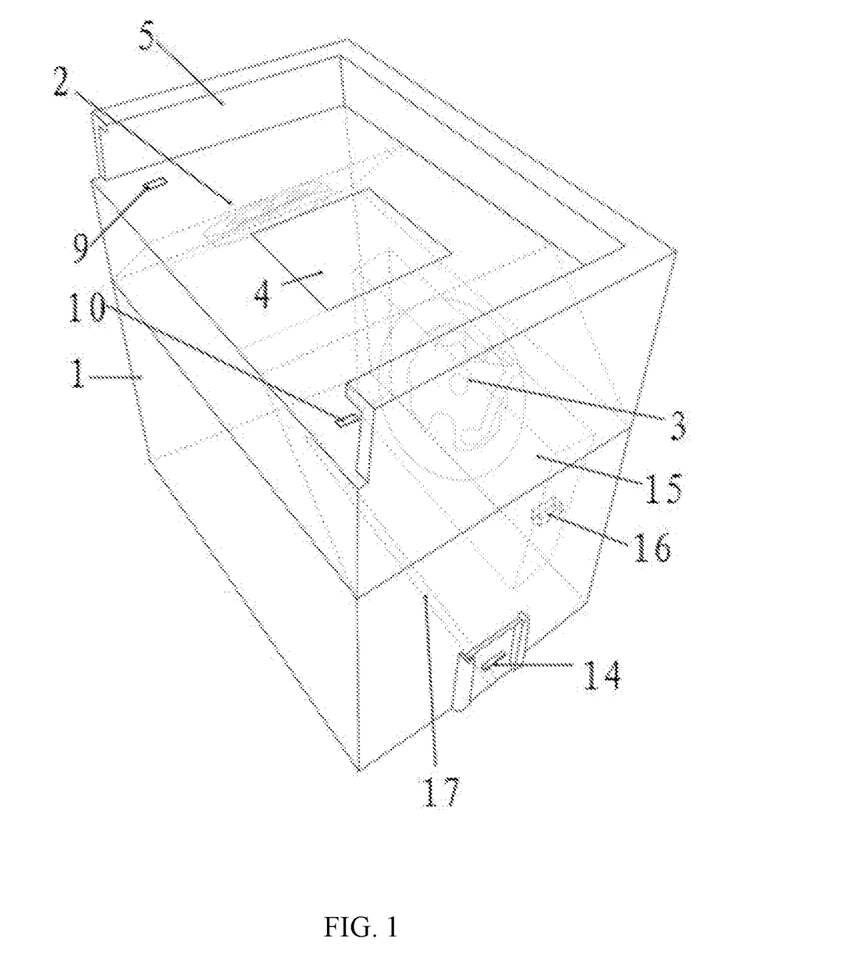
FIG. 1 is a perspective view of an intelligent point-of-care testing device for mycotoxins based on a quantum dots test strip provided by an embodiment of the present disclosure.

Referring to FIG. 1, an intelligent point-of-care testing device for mycotoxins based on a quantum dots test strip provided by an embodiment of the present disclosure includes a quantum dots test strip 20, a shell 1, a first light source 2, a second light source 3, a light filtering component 4, a clamping component 5, an image capturing component 21, and a processor 22. The first light source 2 and the second light source 3 are both arranged inside the shell 1. The first light source 2 and the second light source 3 are opposite to the test strip 20 in the shell 1 and coated with the mycotoxin antigen coupled with the hyperbranched DNA tetrahedron suspension nanomaterial. A top opening is arranged at a top of the shell 1. The light filtering component 4 blocks the top opening. The clamping mechanism 5 is located above the top of the shell 1. The image capturing component 21 is arranged in the clamping mechanism 5, and a camera of the image capturing component 21 is opposite to the light filtering component 4. A signal output end of the image capturing component 21 is in communication with a signal input end of the processor 22. A battery 15 is arranged in the shell 1. A power switch 16 is arranged on the battery 15, and can control the battery 15 and supply power to the first light source 2 and the second light source 3. The light filtering component 4 is used for filtering impurity light.

In this embodiment, the test strip is arranged in a test strip clamping slot 17 at a bottom of the shell 1. The light filtering component 4 is a light filter. The image capturing component is a mobile phone, a tablet computer, and the like.

Figure 2:
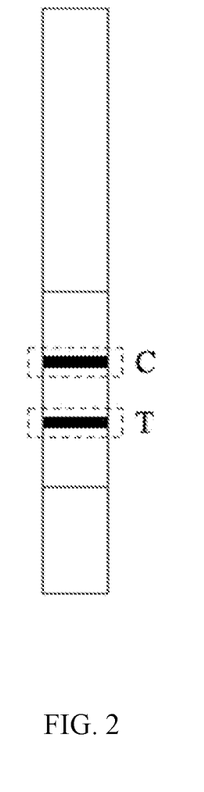
FIG. 2 is a schematic structural diagram of a test strip in an embodiment of the present disclosure.

A specific process for obtaining a mycotoxin content is described. The processor includes:

an image receiving module, configured to receive an image output by the image capturing component;

an image processing module, configured to obtain a fluorescent region of test line T and a fluorescent region of control line C according to the captured fluorescent test strip image, and obtaining red values, green values and blue values of the fluorescent region of test line T and the fluorescent region of control line C respectively;

a normalization module, configured to normalize the red values, green values and blue values of the fluorescent region of test line T and the fluorescent region of control line C to obtain a color normalized value $F_T$ of test line T and a color normalized value $F_C$ of control line C, specifically, referring to FIG. 2, the normalization module including:

a normalization unit, configured to traverse the red values, the green values and the blue values of pixel points of a preset test strip central region row by row, perform normalization to obtain a color normalized value F of each pixel point, and calculate an average value Fa of the color normalized values of the pixel points of each row, wherein for example, the average value of the color normalized values of the pixel points of the first row is Fai, the average value of the color normalized values of the pixel points of the second row is Fat, and the average value of the color normalized values of the pixel points of the nth row is $F_{an}$;

a unit for determining a color normalized value $F_T$ of test line T, configured to determine whether the average value of the color normalized values of the pixel points of certain row A is greater than the average value of the color normalized values of the pixel points of the previous row by a preset threshold; mark row A as a start point of line T if yes; continue to determine whether the average value of the color normalized values of the pixel points of certain row B behind row A is greater than the average value of the color normalized values of the pixel points of the latter row by the preset threshold; mark row B as an end point of line T if yes; and calculate an average value, i.e. the color normalized value $F_T$ of test line T, of the color normalized values of all the pixel points between row A and row B; and a unit for determining a color normalized value $F_C$ of control line C, configured to determine whether the average value of the color normalized values of the pixel points of certain row C behind row B is greater than the average value of the color normalized values of the pixel points of the previous row by the preset threshold; mark row C as a start point of line C if yes; continue to determine whether the average value of the color normalized values of the pixel points of certain row D behind row C is greater than the average value of the color normalized values of the pixel points of the latter row by the preset threshold; mark row D as an end point of line C if yes; and calculate an average value, i.e. the color normalized value $F_C$ of control line C, of the color normalized values of all the pixel points between row C and row D.

an operation module, configured to calculate a mycotoxin content value X according to a standard curve equation Y=a*ln (X)+b, where Y represents a ratio of $F_T$ to $F_C$; a represents a slope of a standard curve linearly fitted according to standard points; and b represents an intercept of the standard curve linearly fitted according to the standard points on the y-axis.

A derivation process of the standard curve equation is described in detail here.

Five test strips with standard toxin concentrations (such as X1 ng/mL, X2 ng/mL>X3 ng/mL, X4 ng/mL, and X5 ng/mL) are respectively put into the test strip slot 17 of the instrument for testing. Captured images are processed to obtain test strip normalized values $F_T$ and control strip normalized values $F_C$ of five standard points. A ratio of $F_T$ to $F_C$ is Y. The natural logarithms Ln (X1), Ln (X2), Ln (X3), Ln (X4) and Ln (X5) of the five standard toxin concentrations are taken as abscissas, and the ratios Y1, Y2, Y3, Y4 and Y5 of $F_T$ to $F_C$ are taken as ordinates. Linear fitting is performed by the least square method to obtain a standard curve equation "Y=a*ln (X)+b", where a represents a slope of a standard curve linearly fitted according to the standard points; and b represents an intercept of the standard curve linearly fitted according to the standard points on the y-axis.

Figure 3:
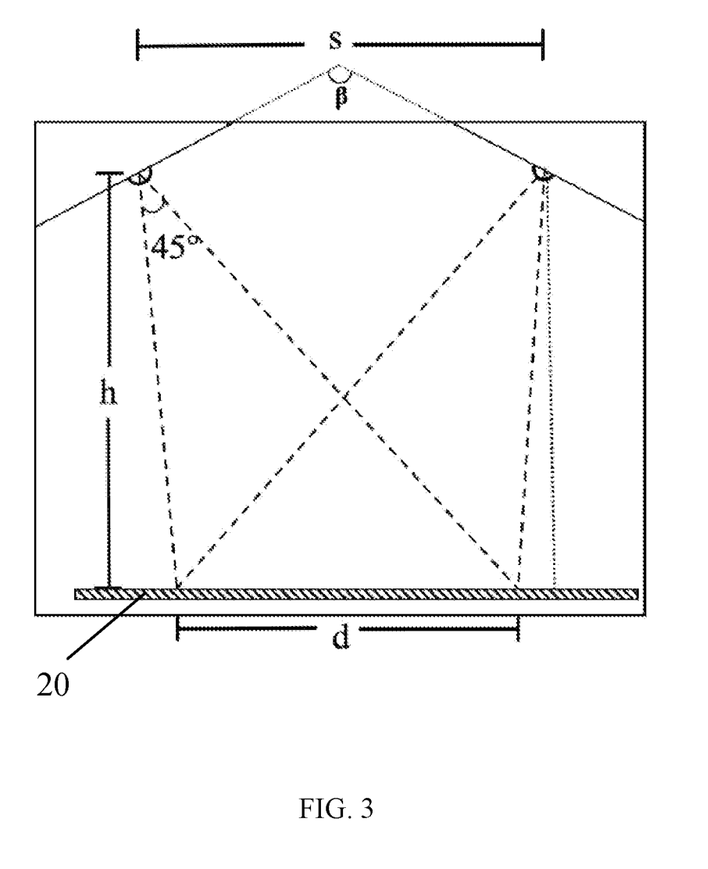
FIG. 3 is a geometric relationship structural diagram of a first light source 2 and a second light source 3 in the intelligent point-of-care testing device for mycotoxins based on a quantum dots test strip provided by an embodiment of the present disclosure.

A position relationship between the first light source 2 and the second light source 3 in the shell 1 is described in detail. Referring to FIG. 3, the first light source 2 and the second light source 3 are arranged in the shell 1 in a manner of forming an included angle β. The β is determined according to $$\tan\left(90 - \frac{\beta + 45}{2}\right) = \frac{s - d}{2h},$$

where s is a transverse distance between the first light source 2 and the second light source 3; d is a transverse distance of the emitted light of the first light source 2 or the second light source 3 irradiating the test strip region; and h is a perpendicular distance from the first light source 2 or the second light source 3 to the test strip region.

Specifically, the first light source 2 and the second light source 3 are composed of two light-emitting diode (LED) lamp beads. On the premise that the illumination range of the light sources can cover a testing region of the test strip, in order to make the light sources more concentrated and have higher excited light intensity, the LED lamp beads have a light emission angle of 45° in this embodiment. β is 115°, and h≥6.5 cm, so that the camera can focus.

Figure 4:
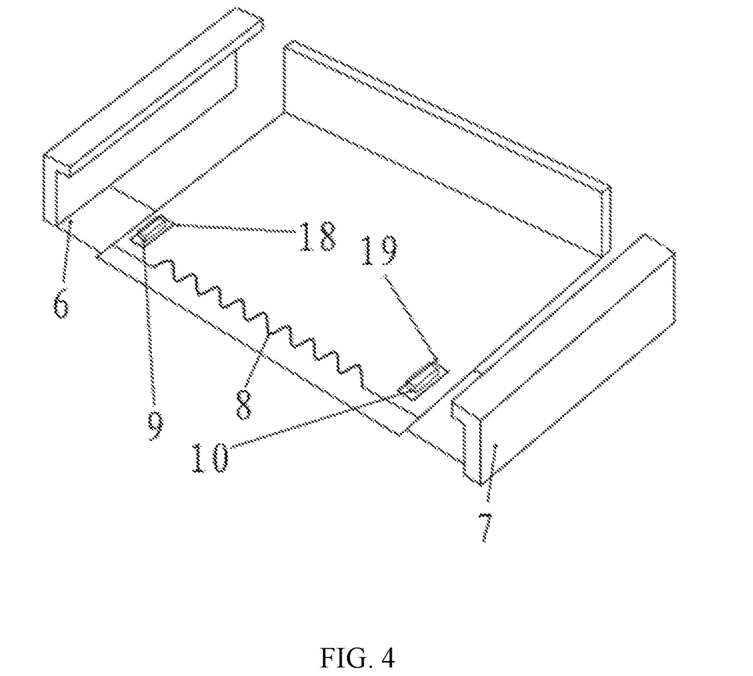
FIG. 4 is a three-dimensional diagram of a clamping mechanism 5 in the intelligent point-of-care testing device for mycotoxins based on a quantum dots test strip provided by an embodiment of the present disclosure.
Figure 5:
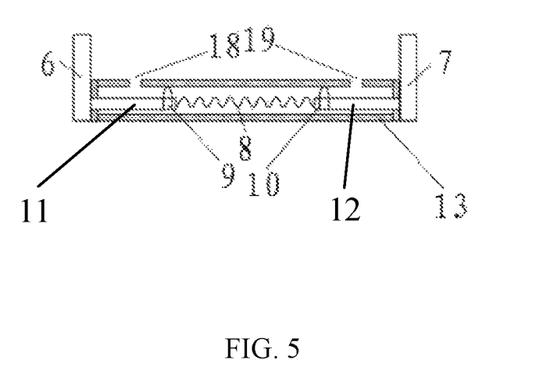
FIG. 5 is a front sectional view of the clamping mechanism 5 in the intelligent point-of-care testing device for mycotoxins based on a quantum dots test strip provided by an embodiment of the present disclosure in an initial state.
Figure 6:
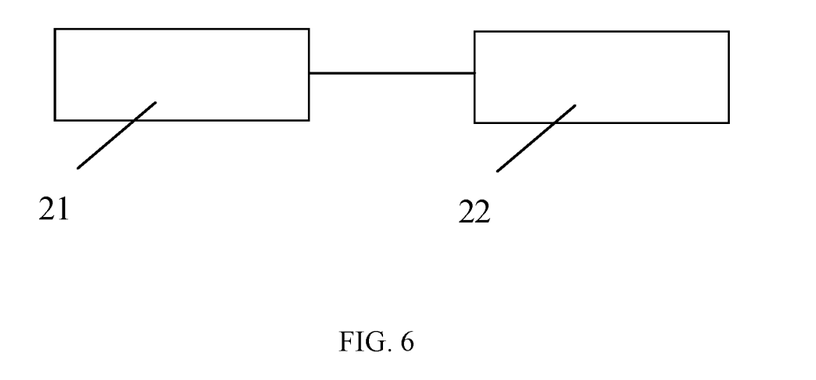
FIG. 6 is a front sectional view of the clamping mechanism 5 in the intelligent point-of-care testing device for mycotoxins based on a quantum dots test strip provided by an embodiment of the present disclosure in an active state.

The structure of the clamping mechanism 5 is described in detail. Referring to FIG. 4 to FIG. 6, the clamping mechanism 5 includes a first L-shaped splint 6, a second L-shaped splint 7, an elastic component 8, a first bulge 9, a second bulge 10, a first elastic base 11, a second elastic base 12, and a cavity body 13. The first L-shaped splint 6 and the second L-shaped splint 7 are respectively arranged on both sides of the cavity body 13. A horizontal portion of the first L-shaped splint 6 is connected with a horizontal portion of the second L-shaped splint 7 through the elastic component 8. The elastic component 8 passes through the cavity body 13. Both ends of an upper wall of the cavity body 13 are respectively provided with a first opening 18 and a second opening 19. The first bulge 9 is vertically arranged on the first elastic base 11, and the first elastic base 11 is arranged on the horizontal portion of the first L-shaped split 6. The second bulge 10 is vertically arranged on the second elastic base 12, and the second elastic base 12 is arranged on the horizontal portion of the second L-shaped split 7.

Before testing, the first L-shaped splint 6 and the second L-shaped splint 7 are pulled towards opposite directions, that is, the first bulge 9 and the second bulge 10 are pulled towards the opposite directions, until the first L-shaped split and the second L-shaped split respectively move to positions below the first opening 18 and the second opening 19. At this time, the first elastic base 11 and the second elastic base 12 respectively push the first bulge 9 and the second bulge 10 upward and fix same through the first opening 18 and the second opening 19. When the image capturing component is placed on the upper wall of the cavity body 13, the first bulge 9 and the second bulge 10 are pressed due to the gravity of the image capturing component, so that the first elastic base 11 and the second elastic base 12 are compressed, and the first bulge 9 and the second bulge 10 retract back into the cavity body 13 to release the fixation. The first L-shaped splint 6 and the second L-shaped splint 7 move towards each other under the action of the contractability of the elastic component 8 until the image capturing component is clamped tightly and fixed at the position of the image capturing component. After the image capturing component is fixed at its position, its image capturing position is also fixed, which is conducive to improving the stability and accuracy of image capturing, thus reducing a testing error.

In order to stably clamp the image capturing component and avoid the abrasion of the side portion of the image capturing component, inner walls of the first L-shaped splint 6 and the second L-shaped splint 7 are provided with antiskid flexible materials.

In this embodiment, the antiskid flexible material is rubber.

The structure of the intelligent point-of-care testing device for mycotoxins based on a quantum dots test strip provided by the embodiment of the present disclosure is described in detail, which also includes a light shield door 14. A side opening is arranged at the side portion of the shell 1. The light shield door 14 is arranged at the side opening.

The arrangement of the light shield door 14 is described in detail. The light shield door 14 is hinged to or slidably connected to the side opening.

A preparation process of a mycotoxin antigen sprayed to the test strip and coupled with a hyperbranched DNA tetrahedron suspension nanomaterial in the embodiment of the present disclosure is described in detail:

The mycotoxin antigen coupled with a hyperbranched DNA tetrahedron suspension nanomaterial on the test strip is prepared by coupling a hyperbranched high-molecular polymer with a DNA tetrahedron connected with an initiator and then coupling the whole with an antigen.

Specifically, the preparation achieved by coupling a hyperbranched high-molecular polymer with a DNA tetrahedron connected with an initiator and then coupling the whole with an antigen includes:

Reaction is enabled between polyethylene glycol methyl ether methacrylate high-molecular polymer having a side chain and the DNA tetrahedron connected with an initiator at 95° C. for 2-3 minutes, and then quenching is performed in an ice bath for 30 seconds to 1 minute for coupling to form the DNA tetrahedron suspension nanomaterial;

a mycotoxin antigen is coupled to the DNA tetrahedron suspension nanomaterial to obtain a DNA tetrahedron suspension nanomaterial-antigen conjugate; and the DNA tetrahedron suspension nanomaterial-antigen conjugate is sprayed to line T of the test strip.

In this embodiment, an initiator DNA sequence and a DNA tetrahedron suspension nanomaterial synthesis sequence are as shown in Table 1.

TABLE 1

Initiator DNA and DNA tetrahedron suspension nanomaterial synthesis sequence

| Name | Initially fitted sequence (5'-3') |
|---|---|
| S1 | 5'-TAGTCGAACGTACACTAAGCTCGCTTGTAAGG-ATC GTA CGA TCA TAG ATC AAT-COOH-3' (SEQ ID NO: 1) |
| S2 | 5'-AAGTCATGCTAGCCTAATAAACATTAGCTG *TCTTCGGCCTCTGTATAGCCACCTACTGACG-*TAC AGT CGT ATT GCA TTC CGA-COOH-3' (SEQ ID NO: 2) |
| S3 | 5'-GACTACCTGCTACACGAAGGCTAGCATGAC TTT*TCCTTACAAGCGAGCTA*GACGACATGACTCT *GTGCAATGATATACTGAACTGATCCATTCGA-*ATT CTA GAC GTT ACT TAA CAA-COOH-3' (SEQ ID NO: 3) |
| S4 | 5'-CAGCTAATGTTTATACGTGTAGCAGGTAGTC *TCGAATGGATCAGTACTATACGGGAAGAGC-*TAA CTA TAG CTA CAA GCT TTC-3' (SEQ ID NO: 4) |
| S5 | 5'-ATAGCTCATCCGGCTCAATA*CAGAGGC CGAAGA-* CCA TAC CGC CAT TTC CAA CTA-COOH-3' (SEQ ID NO: 5) |
| S6 | 5'-AGAGTCATGTCGTCAAGTGTACGTTCGACTA *CGTCAGTAGGTGGCA*GAGCCGGATGAGCTATG*CT CTTCCCGTATAGATTTTTTAGTAGGTGGTAGAG* (SEQ ID NO: 6) |
| S7 | 5'-CAGTATATCATTGCAC-AAG CAC ATG CGA TGT TTA ACT-COOH-3' (SEQ ID NO: 7) |
| Initiator DNA | 5'-ATRP-Initiator-CTCTACCACCTAC-3'(SEQ ID NO: 8) |

In order to improve the orderliness and identifiability of the antigen and make the test strip have higher stability and longer shelf life, after the DNA tetrahedron suspension nanomaterial-antigen conjugate is sprayed to line T of the test strip, the preparation process further includes:

the coated test strip is dried in a vacuum drying oven at 38° C. for 30-60 minutes, and is sealed without light for preservation and later use.

A mycotoxin analysis process performed through the intelligent point-of-care testing device for mycotoxins based on a quantum dots test strip provided by the embodiment of the present disclosure is as follows:

A smart phone is put in the clamping mechanism 5. The light shield door 14 is opened. The test strip coated with the mycotoxin antigen coupled with the hyperbranched DNA tetrahedron suspension nanomaterial is put into the test strip slot 17 of the shell 1, and the light shield door 14 is the closed. The power switch 16 of the built-in battery 15 is turned on, and the first light source 2 and the second light source 3 will then be turned on to project the excited light to the test strip. A fluorescent substance pre-coated on the test strip emits fluorescent light under the excitation of the excited light. The smart phone captures the image information of the fluorescent test strip through the light filtering component 4, and the image of the fluorescent test strip is then processed and converted into digital information substituted into the preset standard curve equation to calculate a mycotoxin result.

Embodiment 1 (Agricultural Food)

Test on Aflatoxin and Zearalenone in Maize:

60 g of niblets are weighed, and 60 mL of acetonitrile/aqueous solution (80:20, v:v) is added; homogenization is performed at 18000 rpm for 2 minutes, and the mixture is filtered with glass fiber filter paper. The filtrate is collected. 3 mL of a sample diluent (which is a PBS buffer solution containing 1% BSA, 1% saccharose, 2% tween-20, and 0.5% PVPK-30, with the pH of 7.4, 0.01 M) is added into 1 mL of the filtrate. 200 μL of the mixed solution and 1 μL of a quantum dots fluorescence probe are added into an enzyme-labeled micropore, and the mycotoxin quantum dots test strip is plugged for incubation at 37° C. for 6 minutes. The test strip is taken out, and is plugged into the test strip clamping slot 17 of the shell 1. The smart phone is used for capturing images for image data acquisition and conversion to obtain contents of the aflatoxin and zearalenone in the maize.

Embodiment 2 (Life Health)

Test on Aflatoxin and Zearalenone in Urine:

10 mL of urine is filtered with quantitative filter paper. 1 mL of a sample diluent (which is a PBS buffer solution containing 2% BSA, 2% saccharose, 4% tween-20, and 1% PVPK-30, with the pH of 7.4, 0.02 M) is added into 1 mL of the filtered urine. 200 μL of the mixed solution and 1 μL of a quantum dots fluorescence probe are added into an enzyme-labeled micropore, and the mycotoxin quantum dots test strip is plugged for incubation at 37° C. for 6 minutes. The test strip is taken out, and is plugged into the test strip clamping slot 17 of the shell 1. The smart phone is used for capturing images for image data acquisition and conversion to obtain contents of the aflatoxin and zearalenone in the urine.

Technical Effects:

1. The first light source 2 and the second light source 3 are used for exciting the test strip which is placed in the shell 1 and coated with the mycotoxin antigen coupled with the hyperbranched DNA tetrahedron suspension nanomaterial to obtain the emitted light, and the light filtering component 4 is used for filtering out the impurity light. The clamping mechanism 5 is used for clamping and fixing the image capturing component. The image capturing component is used for capturing an image of the mycotoxin quantum dots test strip. The processor is used for analyzing and calculating image information to obtain a mycotoxin content result. The traditional testing method is not used. The testing time is shortened, and the portability and practicability of mycotoxin testing are improved. Quantitative instant testing of multi-toxin mixed pollution is achieved, and the technical problem of fluorescence quantification is solved.

2. By the arrangement of the first L-shaped splint 6, the second L-shaped splint 7, the elastic component 8, the first bulge 9, the second bulge 10, the first elastic base 11, the second elastic base 12, and the cavity body 13, a distance between the first L-shaped splint 6 and the second L-shaped splint 7 is adjustable, so that the intelligent point-of-care testing device for mycotoxins based on a quantum dots test strip provided by the embodiment of the present disclosure can be applicable to image capturing components in more sizes and has a wider application range.

3. The inner walls of the first L-shaped splint 6 and the second L-shaped splint 7 are provided with the antiskid flexible materials, so that stable clamping of the image capturing component is achieved, and the abrasion of the side portion of the image capturing component is avoided.

4. The embodiment of the present disclosure further discloses a hyperbranched DNA tetrahedron polymer connected antigen which modifies and strengthens the test line (line T) on the test strip, so that the orderliness and identifiability of the antigen are improved, and the test strip has higher stability and longer shelf life.

Those skilled in the art should understand that the embodiments of the present disclosure may provide a method, a system or a computer program product. Therefore, the present disclosure may adopt the form of a complete hardware embodiment, a complete software embodiment, or a software and hardware combination embodiment. In addition, the present disclosure may adopt the form of a computer program product implemented on one or multiple computer-sensitive storage media (including, but not limited to, a magnetic disk memory, a Compact Disc Read-Only Memory (CD-ROM), an optical memory and the like) including computer-sensitive program codes.

The present disclosure is described by referring to flow diagrams and/or block diagrams of methods, devices (systems) and computer program products according to the embodiments of the present disclosure. It should be understood that computer program instructions may implement each flow and/or each block in the flow diagrams and/or the block diagrams and combination of the flows and/or the blocks in the flow diagrams and/or the block diagrams. These computer program instructions may be provided for a general computer, a dedicated computer, an embedded CPU or processing units of other programmable data processing apparatuses to generate a machine, thereby making the instructions that are executed by the computer or the processing units of other programmable data processing apparatuses generate apparatuses for realizing specified functions in one or multiple flows of the flow diagrams and/or one or multiple blocks of the block diagrams.

These computer program instructions can be stored in a computer-readable memory that can instruct the computer or the another programmable data processing device to work in a specific way, so that the instructions stored in the computer-readable memory generate an artifact that includes an instruction apparatus. The instruction apparatus implements a specified function in one or more processes in the flowcharts and/or in one or more blocks in the block diagrams.

These computer program instructions also may be loaded onto the computer or other programmable data processing apparatuses to execute a series of operation steps on the computer or other programmable data processing apparatuses to generate computer implemented processing, so that the instructions executed on the computer or other programmable data processing apparatuses provide steps for realizing the specified functions in one or multiple flows of the flow diagrams and/or one or multiple blocks of the block diagrams.

Although the preferred embodiments of the present disclosure have been described, those skilled in the art can make other changes and modifications to these embodiments once they acquire the basic creative concept. Therefore, attached claims is intended to be explained as including the preferred embodiments and all the changes and modifications that fall within the scope of the present disclosure.

Obviously, those skilled in the art can make various changes and modifications to the present disclosure without departing from the spirit and scope of the present disclosure. Therefore, if these changes and transformations of the present disclosure fall within the scope of the claims of the present disclosure and equivalent technologies of the present disclosure, the present disclosure is intended to include these changes and transformations.

What is claimed is:

1. An intelligent point-of-care testing device for mycotoxins based on a quantum dots test strip, comprising a test strip, a shell, a first light source, a second light source, a light filtering component, a clamping component, an image capturing component, and a processor, wherein the first light source and the second light source are both arranged inside the shell; the test strip is coated with a mycotoxin antigen coupled with a hyperbranched DNA tetrahedron suspension nanomaterial; the first light source and the second light source are opposite to the test strip in the shell; a top opening is arranged at a top of the shell; the light filtering component blocks the top opening; the clamping component is located above the top of the shell; the image capturing component is arranged in the clamping component, and a camera of the image capturing component is opposite to the light filtering component; a signal output end of the image capturing component is in communication with a signal input end of the processor;

the clamping component comprises a first L-shaped splint, a second L-shaped splint, an elastic component, a first bulge, a second bulge, a first elastic base, a second elastic base, and a cavity body; the first L-shaped splint and the second L-shaped splint are respectively arranged on both sides of the cavity body; a horizontal portion of the first L-shaped splint is connected with a horizontal portion of the second L-shaped splint through the elastic component; the elastic component passes through the cavity body; both ends of an upper wall of the cavity body are respectively provided with a first opening and a second opening; the first bulge is vertically arranged on the first elastic base, and the first elastic base is arranged on the horizontal portion of the first L-shaped split; the second bulge is vertically arranged on the second elastic base, and the second elastic base is arranged on the horizontal portion of the second L-shaped split; inner walls of the first L-shaped split and the second L-shaped split are provided with antiskid flexible materials, so that stable clamping for the image capturing component is achieved, and abrasion of a side portion of the image capturing component is avoided; before testing, the first L-shaped splint and the second L-shaped splint are pulled towards opposite directions, that is, the first bulge and the second bulge are pulled towards the opposite directions, until the first L-shaped split and the second L-shaped split respectively move to positions below the first opening and the second opening; the first elastic base and the second elastic base respectively push the first bulge and the second bulge upward and fix the first bulge and the second bulge through the first opening and the second opening; when the image capturing component is placed on the upper wall of the cavity body, the first bulge and the second bulge are pressed due to gravity of the image capturing component, so that the first elastic base and the second elastic base are compressed, and the first bulge and the second bulge retract back into the cavity body to release fixation; the first L-shaped splint and the second L-shaped splint move towards each other under action of the contractability of the elastic component until the image capturing component is clamped tightly and fixed at the position of the image capturing component;

the mycotoxin antigen coupled with the hyperbranched DNA tetrahedron suspension nanomaterial coated on the test strip is prepared by coupling a hyperbranched high-molecular polymer with a DNA tetrahedron connected with an initiator and then coupling with the mycotoxin antigen;

preparation of the test trip coated with the mycotoxin antigen coupled with the hyperbranched DNA tetrahedron suspension nanomaterial comprises:

enabling reaction between polyethylene glycol methyl ether methacrylate high-molecular polymer having a side chain and the DNA tetrahedron connected with the initiator at 95° C. for 2-3 minutes, and then performing quenching in an ice bath for 30 seconds to 1 minute for coupling to form the hyperbranched DNA tetrahedron suspension nanomaterial;

coupling the mycotoxin antigen to the hyperbranched DNA tetrahedron suspension nanomaterial to obtain the mycotoxin antigen coupled with the hyperbranched DNA tetrahedron suspension nanomaterial; and spraying the mycotoxin antigen coupled with the hyperbranched DNA tetrahedron suspension nanomaterial to a test line T of the test strip;

DNA sequences of the hyperbranched DNA tetrahedron suspension nanomaterial are as follows:

a DNA sequence of the initiator

```
S1:
                                    (SEQ ID NO: 1)
5'-TAGTCGAACGTACACTAAGCTCGCTTGTAAG

GATCGTACGATCATAGATCAAT-COOH-3'

S2:
                                    (SEQ ID NO: 2)
5'-AAGTCATGCTAGCCTAATAAACATTAGCTGT

CTTCGGCCTCTGTATAGCCACCTACTGACGTACA

GTCGTATTGCATTCCGA-COOH-3'

S3:
                                    (SEQ ID NO: 3)
5'-GACTACCTGCTACACGAAGGCTAGCATGACT

TTCCTTACAAGCGAGCTAGACGACATGACTCTGT

GCAATGATATACTGAACTGATCCATTCGAATTCT

AGACGTTACTTAACAA-COOH-3'

S4:
                                    (SEQ ID NO: 4)
5'-

CAGCTAATGTTTATACGTGTAGCAGGTAGTCTCG

AATGGATCAGTACTATACGGGAAGAGCTAACTAT

AGCTACAAGCTTTC-3'

S5:
                                    (SEQ ID NO: 5)
5'-ATAGCTCATCCGGCTCAATACAGAGGCCGAA

GACCATACCGCCATTTCCAACTA-COOH-3'

S6:
                                    (SEQ ID NO: 6)
5'-AGAGTCATGTCGTCAAGTGTACGTTCGACTA

CGTCAGTAGGTGGCAGAGCCGGATGAGCTATGCT

CTTCCCGTATAGATTTTTTAGTAGGTGGTAGA

G-3'

S7:
                                    (SEQ ID NO: 7)
5'-CAGTATATCATTGCACAAGCACATGCGATGT

TTAACT-COOH-3'

Initiator DNA:
                                    (SEQ ID NO: 8)
5'-ATRP-Initiator CTCTACCACCTAC-3'.
```

2. The device according to claim 1, wherein the processor is configured to:

outputted by the image capturing component;

obtain a fluorescent region of the test line T and a fluorescent region of control line C according to the image, and obtaining red values, green values and blue values of the fluorescent region of the test line T and the fluorescent region of control line C respectively;

normalize the red values, green values and blue values of the fluorescent region of the test line T and the fluorescent region of control line C to obtain a color normalized value $F_T$ of the test line T and a color normalized value $F_C$ of control line C; and calculate a mycotoxin content value X according to a standard curve equation Y=a*ln (X)+b, where Y represents a ratio of $F_T$ to $F_C$; a represents a slope of a standard curve linearly fitted according to standard points; and b represents an intercept of the standard curve linearly fitted according to the standard points on the y-axis.

3. The device according to claim 2, wherein "normalize the red values, green values and blue values of the fluorescent region of the test line T and the fluorescent region of control line C to obtain a color normalized value $F_T$ of the test line T and a color normalized value $F_C$ of control line C" comprises:

traverse the red values, the green values and the blue values of pixel points of a preset test strip central region row by row, perform normalization to obtain a color normalized value F of each pixel point, and calculate an average value Fa of the color normalized values of the pixel points of each row;

determine whether the average value of the color normalized values of the pixel points of certain row A is greater than the average value of the color normalized values of the pixel points of a previous row by a preset threshold; mark row A as a start point of the test line T if yes; continue to determine whether the average value of the color normalized values of the pixel points of certain row B behind row A is greater than the average value of the color normalized values of the pixel points of the latter row by the preset threshold; mark row B as an end point of the test line T if yes; and calculate an average value, i.e. the color normalized value $F_T$ of the test line T, of the color normalized values of all the pixel points between row A and row B; and determine whether the average value of the color normalized values of the pixel points of certain row C behind row B is greater than the average value of the color normalized values of the pixel points of the previous row by the preset threshold; mark row C as a start point of line C if yes; continue to determine whether the average value of the color normalized values of the pixel points of certain row D behind row C is greater than the average value of the color normalized values of the pixel points of the latter row by the preset threshold; mark row D as an end point of line C if yes; and calculate an average value, i.e. the color normalized value $F_C$ of control line C, of the color normalized values of all the pixel points between row C and row D.

4. The device according to claim 1, wherein the first light source and the second light source are arranged in the shell in a manner of forming an included angle β; and the β is determined according to $$\tan\left(90 - \frac{\beta + 45}{2}\right) = \frac{s - d}{2h},$$

where s is a transverse distance between the first light source and the second light source; d is a transverse distance of the emitted light of the first light source or the second light source irradiating the test strip region; and h is a perpendicular distance from the first light source or the second light source to the test strip region.

5. The device according to claim 1, wherein after the spraying the DNA tetrahedron suspension nanomaterial-antigen conjugate to the test line T of the test strip, the preparation further comprises:

drying the test strip coated with the mycotoxin antigen coupled with the hyperbranched DNA tetrahedron suspension nanomaterial in a vacuum drying oven at 38° C. for 30-60 minutes.

* * * * *

SEQUENCE LISTING

```
Sequence total quantity: 8
SEQ ID NO: 1              moltype = DNA  length = 53
FEATURE                   Location/Qualifiers
source                    1..53
                          mol_type = other DNA
                          note = nanomaterial synthesis sequence
                          organism = Synthetic construct
SEQUENCE: 1
tagtcgaacg tacactaagc tcgcttgtaa ggatcgtacg atcatagatc aat           53

SEQ ID NO: 2              moltype = DNA  length = 82
FEATURE                   Location/Qualifiers
source                    1..82
                          mol_type = other DNA
                          note = nanomaterial synthesis sequence
                          organism = Synthetic construct
SEQUENCE: 2
aagtcatgct agcctaataa acattagctg tcttcggcct ctgtatagcc acctactgac    60
gtacagtcgt attgcattcc ga                                             82
```

-continued

```
SEQ ID NO: 3            moltype = DNA  length = 115
FEATURE                 Location/Qualifiers
source                  1..115
                        mol_type = other DNA
                        note = nanomaterial synthesis sequence
                        organism = Synthetic construct
SEQUENCE: 3
gactacctgc tacacgaagg ctagcatgac tttccttaca agcgagctag acgacatgac    60
tctgtgcaat gatatactga actgatccat tcgaattcta gacgttactt aacaa        115

SEQ ID NO: 4            moltype = DNA  length = 82
FEATURE                 Location/Qualifiers
source                  1..82
                        mol_type = other DNA
                        note = nanomaterial synthesis sequence
                        organism = Synthetic construct
SEQUENCE: 4
cagctaatgt ttatacgtgt agcaggtagt ctcgaatgga tcagtactat acgggaagag    60
ctaactatag ctacaagctt tc                                             82

SEQ ID NO: 5            moltype = DNA  length = 54
FEATURE                 Location/Qualifiers
source                  1..54
                        mol_type = other DNA
                        note = nanomaterial synthesis sequence
                        organism = Synthetic construct
SEQUENCE: 5
atagctcatc cggctcaata cagaggccga agaccatacc gccatttcca acta          54

SEQ ID NO: 6            moltype = DNA  length = 98
FEATURE                 Location/Qualifiers
source                  1..98
                        mol_type = other DNA
                        note = nanomaterial synthesis sequence
                        organism = Synthetic construct
SEQUENCE: 6
agagtcatgt cgtcaagtgt acgttcgact acgtcagtag gtggcagagc cggatgagct    60
atgctcttcc cgtatagatt ttttagtagg tggtagag                            98

SEQ ID NO: 7            moltype = DNA  length = 37
FEATURE                 Location/Qualifiers
source                  1..37
                        mol_type = other DNA
                        note = nanomaterial synthesis sequence
                        organism = Synthetic construct
SEQUENCE: 7
cagtatatca ttgcacaagc acatgcgatg tttaact                             37

SEQ ID NO: 8            moltype = DNA  length = 13
FEATURE                 Location/Qualifiers
source                  1..13
                        mol_type = other DNA
                        note = Initiator
                        organism = Synthetic construct
SEQUENCE: 8
ctctaccacc tac                                                       13
```